United States Patent [19]

Monteleone et al.

[11] Patent Number: 5,258,070
[45] Date of Patent: Nov. 2, 1993

[54] NAIL LACQUER REMOVER COMPRISING PROPYLENE CARBONATE, PROPYLENE GLYCOL AND DIMETHYL ISOSORBIDE

[76] Inventors: Charles Monteleone, 127 Hunnewell Ave., Elmont, N.Y. 11003; Mel Blum, 1385 Lyon Pl., Wantagh, N.Y. 11793; Scott P. Sellitto, 239 Travers Blvd., Amherst, N.Y. 14228

[21] Appl. No.: 911,859

[22] Filed: Jul. 10, 1992

[51] Int. Cl.$^5$ ............................................. C08K 5/04
[52] U.S. Cl. ..................................... 106/311; 252/364
[58] Field of Search ......................... 106/311; 252/366

[56] References Cited

U.S. PATENT DOCUMENTS 4,781,917  11/1988  Luebbe et al. ........................ 424/65

*Primary Examiner*—Mark L. Bell
*Assistant Examiner*—Margaret Einsmann
*Attorney, Agent, or Firm*—Jordan and Hamburg

[57] ABSTRACT

A mixture for the removal of nail lacquer comprises propylene carbonate, propylene glycol and dimethyl isosorbide and, optionally, dimethylsulfoxide.

6 Claims, No Drawings

NAIL LACQUER REMOVER COMPRISING PROPYLENE CARBONATE, PROPYLENE GLYCOL AND DIMETHYL ISOSORBIDE

BACKGROUND OF THE INVENTION

The present invention relates to nail polish remover. Nail polish is frequently called "nail lacquer," especially in the technical literature.

Organic solvents, frequently diluted with water, are commonly used for the removal of nail lacquer, particularly from finger and toe nails. Organic solvents commonly used for this purpose include acetone, methyl ethyl ketone, acetonitrile, ethyl acetate and butyl acetate. These solvents are variously volatile, flammable or toxic, all of which properties clearly are disadvantageous. Moreover, there is a trend toward the prohibition of the inclusion of volatile solvents in consumer products in order to reduce air pollution.

U.S. Pat. No. 4,801,331 (Murase) discloses a nail lacquer remover in the form of a transparent gel containing, among other ingredients, a carbonate selected from the group consisting of ethylene carbonate, propylene carbonate, butylene carbonate and glycerine carbonate and 1,3-dimethyl-2-imidazolidone ("DMI"). The carbonate and DMI are said by Murase to readily dissolve nitrocellulose, which, of course, is the main constituent of a common type of nail lacquer. Other essential ingredients of Murase's nail lacquer remover are hydroxypropyl cellulose and water.

U.S. Pat. No. 4,032,464 discloses an opaque, creamy nail lacquer remover containing, among other ingredients, about 70 to 90% by weight of acetone and about 1% by weight of propylene glycol or glycerine as a humectant.

Dimethyl isosorbide is known as a dermal penetrant, solvent for pharmaceuticals and coupling agent to aid preparation of a homogeneous deodorant stick but these have nothing to do with nail lacquer removal. Typical prior art relating to dimethyl isosorbide is: U.S. Pat. Nos. 3,699,230, 4,032,464, 4,228,162, 4,711,904, 4,781,917, 4,801,331 and 4,816,261 as well as PCT Published Application No. WO 89/04179.

SUMMARY OF THE INVENTION

According to the invention, it has been found that a mixture of propylene carbonate, propylene glycol and dimethyl isosorbide is a highly effective nail lacquer remover which is neither volatile nor flammable nor toxic. Further advantages of the propylene carbonate, propylene glycol and dimethyl isosorbide mixtures of the invention are that they are biodegradable, hypoallergenic and do not dry out or otherwise harm nails and cuticles. It is believed that the dimethyl isosorbide functions as a catalyst to render the mixture of propylene carbonate and propylene glycol therewith effective as a solvent for nail lacquer of any type, including those which are based on nitrocellulose or an acrylic polymer or other polymer. Neither propylene carbonate nor propylene glycol individually or in admixture together or individually in admixture with dimethyl isosorbide are found to be solvents for nail lacquer.

Further according to the invention, it has been found that the inclusion of dimethyl sulfoxide ("DMSO") with the foregoing mixture enhances the rate at which the nail lacquer is dissolved, particularly in the case of acrylic polymer based nail lacquers. DMSO is found to be a solvent for nail lacquer, particularly acrylic polymer based nail lacquers, but does not sufficiently rapidly dissolve the nail lacquer to be desirable in and of itself as a nail lacquer remover. Mixtures according to the invention containing DMSO have the same desirable properties enumerated above for mixtures according to the invention not containing DMSO. While undiluted DMSO will dry out cuticles, that effect is not observed for mixtures according to the invention containing DMSO.

DETAILED DESCRIPTION OF THE INVENTION

In a mixture of the invention, the weight ratio of propylene carbonate to propylene glycol preferably is in the range 20:1 to 1:2, the propylene carbonate and propylene glycol together comprising preferably at least about 40% by weight of the mixture. (All percentages stated in this application are by weight, based on the weight of the entire mixture.) When DMSO is included in the mixture, the proportion thereof is preferably about 5 to 30%. For the sake of economy, the mixture typically includes about 5 to 30% by weight water, the water being merely a diluent. For aesthetic purposes, the mixture typically includes small proportions of fragrance and dye, for example about 0.05 to 1% by weight fragrance and about 0.01 to 0.1% by weight dye. The mixtures may contain a minor proportion of ethanol, for example 5%. While the dimethyl isosorbide is miscible in water, dissolving it in ethanol prior to its addition to water avoids possible separation of water and dimethyl isosorbide into separate phases which would necessitate subsequent vigorous mixing to provide homogeneity. Other optional constituents include aloe vera, for example about 1 to 5% by weight, and water soluble tocopherol, typically about 0.05 to 1% by weight. Aloe vera and tocopherol moisturize and aid the healing of irritated or damaged cuticles. Tocopherol is also believed to promote nail growth.

The most preferred mixtures of the invention comprise about 50 to 90% by weight propylene carbonate, about 4 to 35% by weight propylene glycol, about 1 to 30% by weight dimethyl isosorbide and, optionally, about 5 to 30% by weight DMSO. Typical commercially preferred formulations are about 50 to 80% by weight propylene carbonate, about 5 to 30% by weight propylene glycol, about 1 to 25% dimethyl isosorbide, about 5 to 25% DMSO, about 0.05 to 1% by weight fragrance, about 0.01 to 0.1% by weight dye and about 5 to 30% by weight water.

The following examples of nail lacquer removers further illustrate the invention.

| Example 1 | |
|---|---|
| dimethyl isosorbide | 5% by weight |
| propylene glycol | 10% by weight |
| de-ionized water | 5% by weight |
| propylene carbonate | 80% by weight |
| Example 2 | |
| dimethyl isosorbide | 5% by weight |
| propylene glycol | 10% by weight |
| de-ionized water | 10% by weight |
| propylene carbonate | 75% by weight |
| Example 3 | |
| dimethyl isosorbide | 5% by weight |
| propylene glycol | 10% by weight |
| de-ionized water | 15% by weight |
| propylene carbonate | 70% by weight |
| Example 4 | |
| dimethyl isosorbide | 5% by weight |

| | |
|---|---|
| propylene glycol | 10% by weight |
| de-ionized water | 15% by weight |
| propylene carbonate | 60% by weight |
| DMSO | 10% by weight |

Having now fully described the invention it will be apparent to one of ordinary skill in the art that many changes and modifications can be made thereto without departing from the spirit or scope of the invention as set forth herein.

What we claim is:

1. A mixture for the removal of nail lacquer, comprising propylene carbonate, propylene glycol and dimethyl isosorbide, in which the propylene carbonate and propylene glycol are in the mixture in a weight ratio of propylene carbonate to propylene glycol in the range 20:1 to 1:2, the propylene carbonate and propylene glycol comprise collectively at least about 40% by weight of the mixture, and the dimethyl isosorbide comprises about 1 to 30% by weight of the mixture.

2. A mixture according to claim 1, further comprising dimethyl sulfoxide in a proportion of about 5 to 30% by weight of the mixture.

3. A mixture for the removal of nail lacquer, comprising propylene carbonate, propylene glycol and dimethyl isosorbide, in which the propylene carbonate and propylene glycol comprise at least about 40% by weight of the mixture.

4. A mixture according to claim 3, in which the weight ratio of propylene carbonate to propylene glycol is in the range of 20:1 to 1:2.

5. A mixture for the removal of nail lacquer, comprising about 50 to 95% by weight of propylene carbonate, about 4 to 35% by weight of propylene glycol and about 1 to 30% by weight of dimethyl isosorbide.

6. A mixture for the removal of nail lacquer, comprising about 50 to 90% by weight of propylene carbonate, about 4 to 35% by weight of propylene glycol, about 5 to 30% by weight of dimethyl sulfoxide and about 1 to 30% by weight of dimethyl isosorbide.

* * * * *